United States Patent
Lorenz et al.

(10) Patent No.: US 10,501,406 B2
(45) Date of Patent: Dec. 10, 2019

(54) LOW BY-PRODUCT CONTENT POLYPHENYLENE POLYMETHYLENE POLYISOCYANATES

(71) Applicant: BASF SE, Ludwigshafen (DE)

(72) Inventors: Michael Lorenz, Ludwigshafen (DE); Axel Franzke, Duesseldorf (DE); Robert Baumann, Mannheim (DE); Michael Bock, Ruppertsberg (DE); Geert Janssens, Nieuwkerken-Waas (BE)

(73) Assignee: BASF SE, Ludwigshafen (DE)

( * ) Notice: Subject to any disclaimer, the term of this patent is extended or adjusted under 35 U.S.C. 154(b) by 47 days.

(21) Appl. No.: 15/546,871

(22) PCT Filed: Jan. 22, 2016

(86) PCT No.: PCT/EP2016/051339
§ 371 (c)(1),
(2) Date: Jul. 27, 2017

(87) PCT Pub. No.: WO2016/120167
PCT Pub. Date: Aug. 4, 2016

(65) Prior Publication Data
US 2018/0009742 A1    Jan. 11, 2018

(30) Foreign Application Priority Data
Jan. 30, 2015  (EP) ..................... 15153238

(51) Int. Cl.
| C07C 263/04 | (2006.01) |
| C07C 269/04 | (2006.01) |
| C07C 265/14 | (2006.01) |
| C07C 271/28 | (2006.01) |
| C08G 18/76 | (2006.01) |
| G01R 33/46 | (2006.01) |

(52) U.S. Cl.
CPC .......... *C07C 263/04* (2013.01); *C07C 265/14* (2013.01); *C07C 269/04* (2013.01); *C07C 271/28* (2013.01); *C08G 18/7692* (2013.01); *G01R 33/46* (2013.01)

(58) Field of Classification Search
CPC ... C07C 263/04; C07C 265/14; C07C 269/04; C07C 271/28; C08G 18/7692
See application file for complete search history.

(56) References Cited

U.S. PATENT DOCUMENTS

| 3,155,699 A | 11/1964 | Powers |
| 3,373,182 A | 3/1968 | Powers |
| 3,458,558 A | 7/1969 | Cheng |
| 3,646,096 A | 2/1972 | Horn |
| 3,759,971 A | 9/1973 | Cuscurida et al. |
| 4,146,727 A * | 3/1979 | Shawl .................. 560/25 |
| 4,292,254 A | 9/1981 | Leonard |
| 4,388,246 A | 6/1983 | Sundermann et al. |
| 5,138,015 A | 8/1992 | Yagii et al. |
| 5,773,643 A | 6/1998 | Yagii et al. |
| 6,411,778 B1 | 6/2002 | Peterson |
| 2003/0055282 A1 | 3/2003 | Bosman et al. |
| 2011/0054211 A1 | 3/2011 | Shinohata et al. |

FOREIGN PATENT DOCUMENTS

| DE | 23 43 658 A1 | 3/1975 |
| DE | 25 17 301 A1 | 11/1975 |
| DE | 26 31 168 A1 | 1/1978 |
| DE | 29 33 601 A1 | 3/1981 |
| DE | 288 599 A5 | 4/1991 |
| EP | 0 482 490 A2 | 4/1992 |
| EP | 0 508 714 A2 | 10/1992 |
| EP | 0 524 507 A1 | 1/1993 |
| EP | 1 259 480 A1 | 11/2002 |
| EP | 1 259 480 B1 | 10/2005 |
| FR | 1 399 506 A | 5/1965 |
| GB | 1 384 065 A | 2/1975 |
| GB | 1 459 691 A | 12/1976 |
| JP | 1-203356 A | 8/1989 |

(Continued)

OTHER PUBLICATIONS

International Preliminary Report on Patentability dated May 29, 2017 in PCT/EP2016/051339 (English translation).

(Continued)

*Primary Examiner* — Pancham Bakshi
*Assistant Examiner* — Mark R Luderer
(74) *Attorney, Agent, or Firm* — Oblon, McClelland, Maier & Neustadt, L.L.P.

(57) ABSTRACT

The invention relates to polyphenyl polymethylene polyisocyanates having an NCO number of at least 29% comprising less than 2% by weight ureas, less than 8% by weight carbodiimides or uretonimines and less than 1000 ppm organic chlorine compounds.
The polyphenyl polymethylene polyisocyanates can be prepared according to the invention by reacting
(i) polyphenyl polymethylene polyamines with organic carbonates to give the corresponding polyphenyl polymethylene polycarbamates,
(ii) by thermally cleaving the polyphenyl polymethylene polycarbamates to give the polyphenyl polymethylene polyisocyanates,
wherein, prior to the thermal cleavage, the free amino groups or urea groups present in the carhamate crude mixture comprising the polyphenyl polymethylene polycarbamates are reacted with a derivatizing reagent to give amide groups or urethane groups.
The polyphenyl polymethylene polyisocyanates can further be prepared according to the invention, prior to the thermal cleavage, by removing compounds having free amino groups or urea groups present in the carbamate crude mixture from the carbamate crude mixture by filtration of the carbamate crude mixture comprising the polyphenyl polymethylene polycarbamates over a solid acidic adsorbent in the presence of an acid dissolved in the carbamate crude mixture.

10 Claims, No Drawings

(56) References Cited

FOREIGN PATENT DOCUMENTS

| WO | WO 98/54128 A1 | 12/1998 |
| WO | WO 2009/115538 A1 | 9/2009 |
| WO | WO 2011/051314 A1 | 5/2011 |
| WO | WO 2011/089098 A1 | 7/2011 |
| WO | WO 2012/065995 A1 | 5/2012 |
| WO | WO 2012/066001 A1 | 5/2012 |

OTHER PUBLICATIONS

H.J. Twitchett, "Chemistry of the Production of Organic Isocyanates", Chemical Society Reviews, vol. 3, No. 2, 1974, pp. 209-230.
M.V. Moore, "Kirk-Othmer Encyclopedia of Chemical Technology", John Wiley & Sons Inc., vol. 2, No. 3, 1978, pp. 338-348 (with cover page).
International Search Report dated Apr. 13, 2016 in PCT/EP2016/051339.

* cited by examiner

LOW BY-PRODUCT CONTENT POLYPHENYLENE POLYMETHYLENE POLYISOCYANATES

The invention relates to low by-product content polyphenyl polymethylene polyisocyanates and methods for the preparation thereof.

The polyphenyl polymethylene polyisocyanates (generally a mixture of 4,4'-methylenediphenyl diisocyanate, the isomers and higher homologs thereof, abbreviated to pMDI) may be prepared via two routes. Firstly by means of phosgenation of polyphenyl polymethylene polyamines (4,4'-diaminodiphenylmethane with isomers and higher homologs, pMDA) to give pMDI, and secondly by a phosgene-free route starting from pMDA to give polyphenyl polymethylene polycarbamates (4,4'-methylenediphenyldiurethane with isomers and higher homologs, pMDU) and then to give pMDI. The terms "urethane" and "carbamate" are used synonymously hereinafter.

The nature of polyphenyl polymethylene polyamine is largely determined by the ratio of formaldehyde (F) and aniline (A) and is frequently described, for example in H. J. Twichett, Chem. Soc. Rev. 3(2), 209 (1974), DE 2343658 and DE 2517301. Depending on the ratio, a product may be obtained comprising many bicyclic compounds (NF high) or a rather oligomeric product with more formaldehyde. The reactant used for this invention is industry standard polyphenyl polymethylene polyamine, which is also used nowadays for the phosgenation process. This polyphenyl polymethylene polyamine is subjected to the phosgenation and the phosgenation solvent is subsequently removed, generally resulting in an NCO content of 30.0 to 33.5% (crude pMDI).

The term pMDA describes a polymeric aromatic amine which is prepared from the acidic condensation of aniline with formaldehyde. The preparation of MDA and pMDA is generally known and may be prepared by continuous, semi-continuous or batchwise processes. The degree of crosslinking can be adjusted by selection of the stoichiometric ratio of amine to formaldehyde.

This results in a specific ring and isomer distribution for the pMDA. The proportion by weight of the overall mixture for the sum total of the three possible bicyclic isomers is between 30 and 80% by weight. The proportion by weight of the overall mixture for the sum total of the different tricyclic isomers is between 10 and 40% by weight. The proportion by weight of the overall mixture for the sum total of the different tetracyclic isomers is between 2 and 20% by weight. The remaining residue of up to 15% by weight is largely composed of higher-ring isomers and a low proportion of by-products such as 2-ring diquinazolines, N-formyl-MDA, N-methyl-MDA, 3-ring 1-diquinazolines, 3-ring 2-diquinazolines and 4-ring diquinazolines. The process is described in numerous patents and publications (H. J. Twichett, Chem. Soc. Rev. 1974, 2, 209; M. V. Moore in: Kirk-Othmer Encycl. Chem. Technol., 3rd Ed., New York, 2, 338-348 (1978)).

The phosgenation of pMDA in the liquid phase to give pMDI is a very widely used commercial process. However, phosgene is an acutely toxic chemical and, in addition, a complex infrastructure is required for a phosgene method for preparing pMDI from pMDA, which, for example must involve chlorine recycling.

In the reaction of complex polyamine-containing mixtures with phosgene, further chlorine-containing compounds are formed, particularly N,N-disubstituted (secondary) carbamoyl chlorides and chlorinated phenyl isocyanates and higher homologs and isomers thereof. Aromatic halogen compounds should be avoided since, at elevated temperatures, they may be converted chemically into compounds with readily hydrolyzable halogen. However, hydrolyzable halogen compounds disrupt the reaction of isocyanates with polyols to polyurethanes since the reaction rate is influenced by the halogen compounds. Furthermore, halogen compounds cause a rapid yellowing of the resulting initially water-clear and colorless isocyanates.

The hydrolyzable chlorine content can be determined in principle according to ASTM D4663-10 (frequently referred to as "DHC" or difficultly hydrolyzable chlorine). The total chlorine content according to ASTM D 4661-09, which also detects ring-substituted chlorine compounds such as monochlorobenezene, differs from the so-called content of easily hydrolyzable chlorine (EHC) according to ASTM D 5629-05, which recognizes the acidity in the form of HCl. Typically, in the pMDI prepared by the phosgene method, the DHC content is 100-2000 ppm and the EHC content is 20-300 ppm Cl. The overall chlorine content is typically at least 200 ppm.

Methods for preparing MDI having a low chlorine compound content are known from the prior art. Methods are differentiated between those by which distillable MDI (2r-MDI, i.e. 2,2'-MDI, 2,4'-MDI, 4,4'-MDI or mixtures thereof) and non-distillable MDI (pMDI) are dechlorinated. Thus the residual chlorine content achievable in 2r-MDI is significantly lower than in pMDI. This is due to the fact that many of the components can be removed by stripping or rectification. Many chlorinated species, however, are present bound to high molecular weight pMDI chains and thus in non-distillable form.

Additionally, carbodiimides (CDI, R—N=C=N—R) are found in pMDI and their uretonimine conversion products from reaction of carbodiimides with NCO groups. The formation of carbodiimides in pMDI is catalyzed at elevated temperatures by ureas which are present in the pMDI. Ureas form, inter alia, from the reaction of unreacted amines with isocyanates and have a loss of NCO groups and thus lead to isocyanate reactivity in the end product. A carbodiimide is formed by condensation of two isocyanate groups with elimination of carbon dioxide. This reaction takes place at elevated temperature and is catalyzed by ureas.

U.S. Pat. No. 3,458,558 describes a method for purifying organic isocyanates to a chlorine content of less than 50 ppm HC.

WO 2012/065995 and WO 2012/066001 describe a method for dechlorinating 2r-MDI. The chlorine content in the 4,4'-MDI is preferably at most 10 ppm.

U.S. Pat. No. 3,646,096 describes the reduction of chlorine compounds in the 2r-MDI by zinc fatty acid salt (zinc laurate). The HC content after processing is 10 ppm.

U.S. Pat. No. 3,155,699 describes the reduction of the chlorine compound content by means of $FeCl_3$. The lowest HC chlorine content is 10 ppm.

U.S. Pat. No. 3,373,182 describes a method for purifying di- and polyisocyanates, particularly TDI, to attain chlorine contents (HC) in the region of 10 ppm.

EP-A 0 482 490 likewise describes a method for dechlorinating 2r-MDI. The 2r-MDI is depleted down to 20 ppm HC.

FR-A 1 399 506 describes a thermal dechlorination of 2r-MDI with a HC residual content of 56 ppm.

DE-A 26 31 168 describes the preparation of diisocyanates which are adjustable with respect to their chlorine content. In this case an isomeric mixture composed largely of 2,4'- and 4,4'-MDI is firstly freed in a distillation column from the majority of the impurities higher boiling than 4,4'-MDI and then the resulting distillate is freed from the impurities lower boiling than 2,4'-MDI by distillation. The technical solution proposed however is very complex in terms of apparatus. The depletion of the resulting 4,4'-MDI of secondary carbamoyl chlorides is also often inadequate. The HC content is approx. 1300 ppm.

DE-A 29 33 601 describes a method for preparing polymeric MDI and monomeric MDI having a low fraction of uretdiones and hydrolyzable chlorine compounds. In a first stage, bicyclic MDI is separated from pMDI in a thin film evaporator at 175-210° C. The distillate from the thin film evaporator is condensed in the presence of an inert gas and then the MDI isomers are separated from one another by distillation. The 4,4'-MDI thus obtained still however comprises undesired compounds which are more high-boiling than 4,4'-MDI. The method, moreover, cannot always be integrated into an overall process in an economic manner. The HC content is approx. 400-1000 ppm.

GB 1 384 065 describes the reduction of the HC chlorine content of a polymeric pMDI from 3000 to 50 ppm. In this case, however, the NCO content decreases and the viscosity increases.

EP-A 0 524 507 likewise describes the purification of pMDI and mentions a typical HC content of 100 to 2000 ppm. This text describes a method for purifying polyisocyanates having trimethylsilyl groups. The hydrolyzable chlorine (HC) content before purification is approx. 100-2000 ppm. In the example on page 6, depletion from 270 ppm to 220 ppm HC is effected.

U.S. Pat. No. 3,759,971 describes the purification of pMDI using magnesium silicates in which an HC content of 100 ppm is achieved.

GB 1 459 691 describes the depletion of pMDI to 279 ppm HC by means of diethyl sulfate.

DD 288 599 describes a method for reducing the content of chlorine-containing compounds in isocyanates by treatment with carbodiimides and subsequent stripping. Thermal dehalogenation, however, does not lead to complete decomposition of the halogen compounds. Thus, the secondary carbamoyl chlorides cannot be completely removed. In addition, undesired degradation products form due to the high thermal stress on the resulting product. The addition of carbodiimides causes an increase in the molecular weight due to trimerization reactions, in addition to the chlorine reduction specified. The HC content is 2270 ppm.

Urethanes (carbamates) are important intermediates in the phosgene-free synthesis of isocyanates. In this case, the amines are converted into the corresponding carbamates and these are subsequently cleaved thermally and/or catalytically to the corresponding isocyanates and the alcohol bound in the carbamate. The preparation of pMDI moreover frequently includes the condensation of N-phenyl carbamates, obtained by urethanization of aniline, with formaldehyde, in which a mixture of pMDU is obtained as intermediate. pMDI can also be obtained by urethanization of pMDA in the presence of an organic carbonate and a base and subsequent thermolysis.

US 2011/054211 A1 describes a phosgene-free route to prepare isocyanates using diaryl carbonates.

U.S. Pat. No. 6,411,778 describes a method of di- and polyurethanes using aromatic amines and urea or alkyl carbamates.

U.S. Pat. No. 5,138,015 describes the chlorine-free preparation of aliphatic isocyanates from dialkyl carbonates with subsequent thermal cleavage of the carbamates. Aromatic amines can likewise be used. Diisocyanates, which are prepared without phosgene using dialkyl carbonate and thermal cleavage of the carbamates, generally comprise less than 1 ppm chlorine according to the data in this document.

U.S. Pat. No. 5,773,643 describes the chlorine-free preparation (<10 ppm chlorine-containing compounds) of aliphatic diisocyanates based on aliphatic amines and dimethyl carbonate in the presence of a base. Thermal cleavage is effected at a pressure of 1-700 Torr in the presence of a high-boiling solvent.

The abovementioned methods for dechlorination are not practical for use on an industrial scale for dechlorination of the pMDI bottom product. The methods described are not applicable to non-distillable compounds. Reagents for the dechlorination are thus added which no longer need to be removed from the pMDI, or methods are described which refer to distillable products. High thermal stress on the pMDI is also technically inadvisable since the occurrence of by-products is promoted.

The urethanization of the relevant amines, aniline, diaminotoluene or diaminodiphenylmethane for example, proceeds incompletely or, in the case of condensation of N-phenyl carbamates with aqueous formalin solution for example, hydrolysis of a portion of the carbamate groups occurs, so the crude carbamate still has free amino groups. In the subsequent thermal cleavage (thermolysis) of the carbamates to give isocyanates, said free amino groups can react with the isocyanate groups forming ureas. These side reactions may involve considerable losses of yield and, owing to the known poor solubility of urea compounds, can lead to solid deposits in the apparatus used for urethane cleavage which impedes continuous operation of the apparatus. In addition, the presence of ureas in the thermolysis leads to decomposition reactions of the isocyanate, inter alia, to carbodiimides (CDI) and uretonimines, which in turn have negative effects on the quality of the isocyanate as already described.

The harmfulness of residual amines in the carbamate thermolysis is described in U.S. Pat. No. 4,292,254.

The purification of polycarbamates by reaction with a reagent is described in U.S. Pat. No. 4,146,727.

Here, disruptive components are removed from the phosgene-free polyisocyanate synthesis via urethane by reaction with a reagent. The specific reaction of ureas with reagents is not mentioned. The disruptive secondary components according to U.S. Pat. No. 4,146,727 are N-benzyl components and in the urethanization unreacted alkylphenyl carbamates and amines. N-Benzyl compounds are chemically converted with the aid of methyl or ethyl chloroformate.

Furthermore, an NCO number <29% is insufficient for an economic preparation and use of pMDI. The current typical specification range for crude pMDI before the two-ring separation to 2r-MDI (2,2'-MDI, 2,4'-MDI, 4,4'-MDI) and pMDI is in the range of 30.0% to 33.5%. After the 2-ring separation, the NCO content in the bottom product pMDI is typically in the range of 29.5 to 32.5%, depending on the amount distilled off. If the NCO content is below 29%, the reactivity of the isocyanate is lower, and the range of applications is limited. Furthermore, a lower NCO content leads automatically to more by-products (carbodiimides and/or uretonimines), which leads to more crosslinking and ultimately to an increase in viscosity, which leads to a lower flow rate of the pMDI. EP 0 508 714 A2 describes that the current storage period of commercial pMDI can be limited to 6 months, since beyond that the pMDI can no longer be used for certain applications. If the initial viscosity at the start of the storage period is even higher, the storage period in the worst case is further reduced. Without purification of the crude carbamate, an NCO number of >29% is not achievable, since in this case the formation of ureas and carbodiimides, caused by the presence of free amine in the crude carbamate, leads to an NCO loss.

Typical values in commerical pMDI for chlorine-containing compounds are 1000 ppm, 8% by weight for carbodiimides and/or uretonimines and 2% by weight for urea.

The object of the invention is to provide polyphenyl polymethylene polyisocyanates (pMDI) having an NCO number of at least 29%, which is characterized by a particularly low content of by-products such as ureas, carbodiimides and uretonimine conversion products thereof and moreover has a particularly low content of chlorinated by-products.

The object is achieved by polyphenyl polymethylene polyisocyanates having an NCO number of at least 29% comprising less than 2% by weight ureas, less than 8% by weight carbodiimides and/or uretonimines and less than 1000 ppm organic chlorine compounds.

The urea content in the context of the present invention is determined by NMR in which the detection limit of the method is 2% by weight.

The content of aromatic chlorine compounds in the context of the present invention is determined by chlorine value and/or HRMS (high-resolution mass spectrometry) in which the detection limit of the methods is 10 ppm.

Organic chlorine compounds, besides other compounds, are particularly compounds of the formulae 1 to 6:

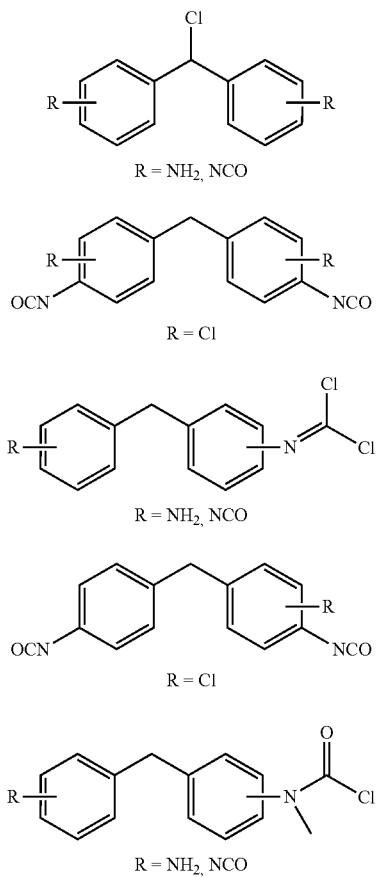

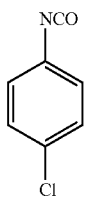

In general, the overall content of the compounds 1 to 6 in the polyphenyl polymethylene polyisocyanates according to the invention is below 100 ppm, preferably below 25 ppm.

The content of carbodiimides and/or uretonimines in the context of the present invention is determined by NMR in which the detection limits of the methods are 2% by weight. Hydrolyzable chlorine can be determined, for example, according to ASTM D4663-10.

The NCO number is determined according to DIN EN ISO 14896.

The NCO content is defined as standard as the percentage mass fraction of NCO groups in a sample.

The polyphenyl polymethylene polyisocyanates according to the invention can be prepared as described below.

In a preferred preparation process
(i) polyphenyl polymethylene polyamines are reacted with organic carbonates to give the corresponding polyphenyl polymethylene polycarbamates,
(ii) the polyphenyl polymethylene polycarbamates are thermally cleaved to give the polyphenyl polymethylene polyisocyanates,
wherein, prior to the thermal cleavage, the free amino groups or urea groups present in the carbamate crude mixture comprising the polyphenyl polymethylene polycarbamates are reacted with a derivatizing reagent to give amide groups or urethane groups.

Organic carbonates can be dialkyl or diaryl carbonates or mixed alkylaryl carbonates; preference is given to dialkyl carbonates.

The crude carbamates are preferably obtained by reacting the polyphenyl polymethylene polyamines with diaryl or dialkyl carbonates in the presence of metal salts or bases. The crude carbamates are particularly preferably obtained by reacting aromatic amines with dialkyl carbonates in the presence of bases, in which in particular metal alkoxides are used as bases. In the latter case, hydrolysis of the intermediate metal carbamate thus obtained follows the actual reaction.

The alcohol R'OH bound in the carbamates can in principle be any alcohol. The alcohol R'OH is preferably an alkanol having 1 to 18 carbon atoms, preferably 1 to 8 carbon atoms, particularly preferably methanol, ethanol, 1-propanol, 1-butanol, 2-methyl-1-propanol, 1-pentanol, 2-methyl-1-butanol or 3-methyl-1-butanol. The alcohol R'OH bound in the carbamates is especially preferably 2-methyl-1-propanol (also called isobutanol).

Also suitable are phenol, mono- or polysubstituted phenols, e.g. with fluorine, or alkyl (methyl, ethyl, propyl, butyl) substituted phenols and also alcohols having heteroatoms, e.g. 2-fluoroethanol, 2,2,2-trifluoroethanol, 1,1,1,3,3,3-hexafluoropropanol, 2-chloroethanol and 2-methoxyethanol.

The crude carbamates are preferably obtained, as described in WO 2009/115538, by reacting aromatic amines with dialkyl carbonates having alkyl residues of 1 to 18, preferably 1 to 8 carbon atoms, in the presence of 0.8 to 1.2 equivalents (eq.) of a base. In this case, the desired urethane is isolated after a short reaction time in yields of up to 98%, even at low excesses of dialkyl carbonate.

The reaction product of the aromatic amine with the dialkyl carbonate in the presence of stoichiometric amounts of a base is subsequently reacted with a protic compound. The protic compound is preferably selected from the group consisting of alcohols, water and mixtures thereof; particular preference is given to water.

The base is preferably used in a molar ratio of 0.8 to 1.2 based on the amino groups. The dialkyl carbonate is preferably used in a molar ratio of dialkyl carbonate to amino groups of from 1:1 to 10:1, more preferably from 2:1 to 7:1. The reaction of the aromatic amine with the dialkyl carbonate in the presence of the base is preferably carried out at a reaction temperature of 60° C. to 150° C., particularly preferably at 90° C. to 140° C. At these temperatures, an essentially quantitative conversion of the aromatic amine to the corresponding urethane can be obtained within 5 min to 300 min. The reaction is typically carried out under standard pressure.

The alkyl chain of the dialkyl carbonate may be unbranched, branched or cyclic. The alkyl chain is preferably branched or unbranched. It is also possible to use mixed residues.

Dimethyl carbonate, bis(trifluoroethyl) carbonate, bis(fluoroethyl) carbonate, bis(2-methoxyethyl) carbonate and bischloroethyl carbonate are suitable.

Examples of diaryl carbonates are diphenyl carbonate, bis(methylphenyl) carbonate, bis(fluorophenyl) carbonate and bis(chlorophenyl) carbonate.

Examples of mixed carbonates are methylphenyl carbonate and methyl trifluoroethyl carbonate.

In a preferred embodiment of the invention the dialkyl carbonates are selected from the group comprising diethyl carbonate, di-n-propyl carbonate, di-n-butyl carbonate, di-2-methylpropyl carbonate, di-3-methylbutyl carbonate, di-n-pentyl carbonate, preferably di-2-methyl propyl carbonate and di-n-butyl carbonate, particularly preferably di-2-methylpropyl carbonate. The dialkyl carbonate can be prepared by reacting ethylene carbonate with an alcohol.

The base preferably comprises basic organic metal compounds, especially compounds of alkali metals. They may, for example, be compounds comprising nitrogen atoms, for example amides such as sodium amide, or compounds comprising silicon atoms and nitrogen atoms, for example lithium hexamethyldisilazide.

The base more preferably comprises the alkoxides of alkali metals. The alcohol of the metal alkoxide preferably has 2-18, particularly preferably 2 to 7, carbon atoms in the alkyl chain. The alkyl chain may be unbranched, branched or cyclic. In a particularly preferred embodiment, the dialkyl carbonates and the metal alkoxides are based on the same alcohol.

It is essential to the invention that, after the urethanization, residual amines present in the carbamate crude mixture are removed from the crude mixture so that no catalytically active ureas can form in the subsequent thermolysis. In this manner, the content of carbodiimide (CDI) and/or uretonimines can be minimized. Furthermore, harmful ureas already present in the crude carbamate are removed by treating the crude carbamate or are rendered harmless by chemical conversion of the ureas in the crude urethane for the subsequent thermolysis.

The crude carbamates produced can have an arbitrarily high proportion of unreacted amino groups and urea groups. However, the proportion of urethane groups, based on the sum total of urethane, amino and urea groups in the crude carbamate product of the urethanization reaction is, before the reaction with a reagent, typically greater than 90%, preferably greater than 95% and particularly preferably greater than or equal to 98%.

The reagent can, in principle, be any compound which essentially reacts completely with the free amino and urea groups present in the crude carbamate to form amide groups or urethane groups or higher substituted (higher substituted=tri- and/or tetrasubstituted) ureas, and which leaves substantially unaltered the urethane groups already present in the crude carbamate.

Higher substituted ureas, i.e. tri- or tetrasubstituted ureas, do not catalyze the formation of carbodiimides.

The conversion of the free amino groups to amide groups and/or the urea groups to higher substituted ureas can be effected, for example, by reaction with esters, acid anhydrides or acyl chlorides, preferably of aliphatic carboxylic acids having 1 to 10 carbon atoms or aromatic carboxylic acids having 7 to 14 carbon atoms, wherein the esters preferably comprise a $C_1$-$C_4$-alkanol as alcohol component, as reagents. The conversion of the free amino groups to urethane groups and/or the urea groups to higher substituted ureas can be effected, for example, by reaction with chloroformic esters or pyrocarbonates, particularly of $C_1$-$C_8$-alkanols, as reagents. The reagents can be mono-, di- or polyfunctional, in which the reaction can go hand in hand with the crosslinking of molecules comprising two or more amino groups.

In one embodiment of the invention, the derivatizing reagent is selected from esters, acid anhydrides and acyl chlorides of aliphatic carboxylic acids having 1 to 6 carbon atoms or aromatic carboxylic acids having 7 to 14 carbon atoms.

Preferred reagents are acetic anhydride, acetyl chloride, propionyl chloride, pivaloyl chloride, benzoyl chloride, malonyl chloride, succinyl chloride, phthaloyl chloride, isophthaloyl chloride, terephthaloyl chloride, succinyl chloride, fumaryl chloride or the chloroformic esters $ClCO_2R'$ or pyrocarbonates $R'OCO_2CO_2R'$ of the abovementioned alcohols R'OH and also benzyl alcohol or 2-methyl-2-propanol.

Particularly preferred derivatizing reagents are selected from acetic anhydride and acetyl chloride.

In a preferred embodiment, the derivatizing reagent is selected from chloroformic esters and pyrocarbonates of $C_1$-$C_8$-alkanols.

Preferred chloroformic esters are isobutyl chloroformate, butyl chloroformate, propyl chloroformate, isopropyl chloroformate, ethyl chloroformate and methyl chloroformate.

Preferred pyrocarbonates are diethyl dicarbonate, dipropyl dicarbonate, diisopropyl dicarbonate, dibutyl dicarbonate and diisobutyl dicarbonate.

The reaction of the free amino groups and/or the urea groups still present in the crude carbamate with the reagents mentioned can be effected in any suitable manner. If the crude carbamates are liquid at the reaction temperature of the reaction, these can be reacted with the reagent in substance, i.e. in the absence of a separate solvent. However, the reaction is preferably carried out in any suitable solvent which is inert under the reaction conditions and does not react with the amino, urea and urethane groups and also not with the reagent. Preferred solvents are aromatic hydrocarbons or chlorohydrocarbons having 6-20 carbon atoms. Particularly preferred solvents are the liquid carbonates used in the urethanization, toluene, xylene, ethylbenzene, mesitylene, chlorobenzene, dichlorobenzene, dichlorotoluene and trichlorobenzene and mixtures thereof. In particular, the same solvent is used which is already employed in the preceding derivatization stage of the urethanization of the aromatic amines to give the crude carbamates and/or in the subsequent thermal cleavage of the crude carbamate to the corresponding isocyanates.

The reagent may be used in an approximately stoichiometric ratio or in excess, based on the amino and urea groups still present in the crude urethane. Monofunctional reagents are preferably used in excess, generally in amounts of 1.0 to 10 equivalents, preferably 1.0 to 5 equivalents and particularly preferably 1.05 to 1.2 equivalents, based on free amino and urea groups in the crude carbamate. Bifunctional or polyfunctional reagents are preferably used in approximately stoichiometric ratios or in a lower excess, generally in amounts of 1.0 to 4 equivalents, preferably 1.05 to 1.2 equivalents of functional groups in the reagent, based on amino and urea groups in the crude carbamate. If an excess of reagent is used, said excess is removed after the reaction has taken place by distillation, is further reacted with e.g. alcohol or is removed by mild hydrolysis e.g. with water.

The excess of reagent is preferably removed from the product mixture by distillation. The reagent removed by distillation can, optionally after a purification step, be subsequently reused and is not lost.

The temperature for the reaction is preferably selected such that the reactions are sufficiently rapid but at the same time does not cause any undesired side reactions, particularly no thermal decomposition of the carbamate groups and/or the reagent. The reaction temperature of the reaction is generally 0 to 160° C., preferably 20 to 100° C. Typically at these temperatures a complete conversion of the amino and urea groups is achieved in 0.1 to 5 h. Preferably, the reaction is carried out at atmospheric pressure or a slight superatmospheric pressure. The pressure is particularly preferably selected to be high enough such that all of the components involved in the reaction and also the solvent are present in liquid form.

The reaction may in principle be carried out continuously or batchwise. The reaction is preferably carried out as a continuous operation. The reaction may be carried out, for example, in one or more stirred tanks or a tubular reactor, or in a combination of one or more stirred tanks and one or more tubular reactors.

The carbamates comprising higher-substituted ureas and essentially amine-free prepared in such a manner are thermally cleaved in a subsequent reaction to give the corresponding isocyanates, optionally after removal of possible excess reagent present and/or adjustment of the amount of solvent by addition of additional solvent or removal of a portion of the solvent, or after solvent exchange.

As an alternative to the process described for the reaction with a reagent, the compounds typically still comprising amino groups and urea groups in the crude product after the urethaneforming reaction are removed by filtration over a solid acidic adsorbent in the presence of an acid. This procedure can be carried out without major problems, even on an industrial scale, with simple apparatus and using a comparatively low amount of adsorbent.

The invention therefore relates to a method for preparing polyphenyl polymethylene polyisocyanates, in which
  (i) polyphenyl polymethylene polyamines are reacted with dialkyl carbonates to give the corresponding polyphenyl polymethylene polycarbamates,
  (ii) the polyphenyl polymethylene polycarbamates are thermally cleaved to give the polyphenyl polymethylene polyisocyanates,
wherein, prior to the thermal cleavage, compounds having free amino groups or urea groups present in the carbamate crude mixture are removed from the carbamate crude mixture by filtration of the carbamate crude mixture comprising the polyphenyl polymethylene polycarbamates over a solid, acidic adsorbent in the presence of an acid dissolved in the carbamate crude mixture.

The method for removing compounds having free amino or urea groups may, in principle, be carried out with a crude carbamate mixture having any high proportion of amino groups and/or urea groups still present. However, the proportion of carbamate groups as a percentage, based on the sum total of carbamate, amino and urea groups in the crude product of the urethanization reaction is, before the filtration, typically greater than 90%, preferably greater than 95% and particularly preferably greater than or equal to 98%.

In order to carry out the filtration, the required amount of acid and optionally at least one solvent is added to the crude carbamate to be purified. The use of an additional solvent is not absolutely necessary but is generally advantageous in order to obtain a homogeneous mixture and to simplify the filtration in terms of the practical procedure. In principle, all substances can be used as solvents which are liquid under the filtration conditions and do not dissolve or attack the solid adsorbent. Preferably used in this case, however, are the common organic solvents familiar to those skilled in the art.

Particular preference is given to using a solvent for the filtration which comprises one or more chlorinated hydrocarbons, such as chlorobenzene, dichlorobenzene (isomerically pure or as an isomeric mixture), trichlorobenzene (isomerically pure or as an isomeric mixture) or dichlorotoluene (isomerically pure or as an isomeric mixture), and also the alcohol R'OH bound in the urethane, where the residue R' is as defined above. With very particular preference, the solvent is, in part or wholly, the same compound which is already used in the preceding stage of urethanization during the reaction and/or the subsequent purification and/or in an optional thermal cleavage of the purified urethanes subsequent to the filtration to give the corresponding isocyanates.

The solid, acidic adsorbent is understood to mean a porous material, insoluble in water and in the medium to be filtered comprising the crude carbamate, the additional acid and optionally at least one solvent, which, owing to its large surface area, can bind particularly polar molecules by physical or chemical forces. An acidic adsorbent generally has functional groups which, under the conditions of adsorption, behave as Brönstedt or Lewis acids. In particular, an acidic adsorbent is capable of preferably retaining basic substances with respect to less basic substances.

Preferred solid, acidic adsorbents are acidic metal oxides such as silicon dioxide, titanium dioxide, aluminum oxide ($Al_2O_3$), boron oxide ($B_2O_3$), zirconium dioxide, silicates, aluminosilicates, borosilicates, zeolites (particularly in their protonated form), ion exchangers, activated carbons and silica gels or mixtures of such substances. Especially preferred solid, acidic adsorbents are silicon dioxide, aluminum oxide ($Al_2O_3$) and silica gel. Very particular preference is given to silica gels, which, for example, can be prepared by acidifying aqueous sodium waterglass solutions and drying the resulting initial silica sols, such as described in Hollemann-Wiberg, Lehrbuch der Anorganischen Chemie (Textbook of Inorganic Chemistry), 102nd edition, Verlag Walter de Gruyter, 2007, page 962. Examples of particularly preferred silica gels are Sorbead WS from BASF SE or silica gel 60 from Merck KGaA.

The filtration of the crude carbamate over the solid, acidic adsorbent in the presence of an acid can be carried out in a continuous or batchwise manner. However, the filtration of the crude product to be purified is preferably carried out continuously. The mixture to be purified is particularly preferably passed over one or more fixed beds or random beds of adsorbent. The fixed bed or random bed are preferably arranged in a tube or a heat exchanger and through which the crude product to be purified generally flows.

The space velocity is preferably 0.01 to 20, particularly preferably 0.05 to 15 and especially preferably 0.1 to 10 kg of mixture to be purified per kg of adsorbent per hour. The fixed bed volumes and the size of the adsorbent particles may vary over a wide range and therefore are adjusted to the chosen reaction conditions and process parameters.

The particle size of the solid, acidic adsorbents used, however, is preferably 0.03 to 10, particularly preferably 0.2 to 6 and especially preferably 1 to 4 mm, since excessively large particles have negative diffusion effects and excessively small particles can lead to blockages in the adsorber. The particles are preferably spherical.

In a preferred embodiment, the adsorbent is in a fixed bed in a carousel arrangement, particularly with regeneration, i.e. the flow is through two or more alternative fixed beds such that the unused fixed beds can be regenerated.

The pressure is generally not critical. However, a pressure is established at which the mixture to be purified is in liquid form. The pressure is generally 1 to 50 bar, preferably not more than 10 bar.

The filtration is generally conducted at temperatures of less than 120° C., preferably less than 90° C. and particularly preferably less than 60° C.

The treatment with adsorbent can be conducted under an inert gas atmosphere, for example, under nitrogen or argon.

If required following the filtration, the adsorbent or parts of the adsorbent, for example abrasion, can be removed by suitable methods from the purified urethane, for example, by filtration, centrifugation or sedimentation.

It may be necessary that the adsorbent has to be regenerated after a certain operating duration if the activity of the adsorbent decreases with increasing operating duration.

The adsorbent can be regenerated preferably by washing with water or a mixture of water and one or more lower alcohols having 1 to 4 carbon atoms, such as methanol, ethanol, 1-propanol, 2-propanol, 1-butanol or 2-methyl-1-propanol. In a preferred embodiment, the washing solution used for the regeneration comprises a low amount of a homogeneously dissolved base, for example, ammonia, sodium hydroxide, sodium carbonate or triethylamine.

During the filtration over the solid, acidic adsorbent, additional acid present takes the form of a Brönstedt acid compound, which is homogeneously dissolved under the conditions of the absorption in the medium used comprising the crude urethane and optionally one or more solvents and is capable of forming the corresponding salts by proton transfer on to the free amine and urea functionalities of the crude urethane. The acid is preferably a compound having a $pK_a$ in water of less than 4. The acid is particularly preferably hydrogen halide such as hydrogen chloride or hydrogen bromide, mineral acids such as phosphoric acid, sulfuric acid or nitric acid, perchloric acid, sulfonic acids such as methanesulfonic acid, phenylsulfonic acid, paratoluenesulfonic acid or trifluoromethanesulfonic acid, or corresponding strong carboxylic acids such as chloroacetic acid, trichloroacetic acid, trifluoroacetic acid or the isomeric nitrobenzoic acids. Very particular preference is given to using hydrogen chloride or methanesulfonic acid.

The aforementioned acidic compounds may be used individually or as mixtures of two or more components. Preferably, however, only one acid is used.

The now amine and urea-free polyphenyl polymethylene polycarbamates (pMDU) purified in such a manner by filtration through a solid stationary phase are cleaved in a subsequent reaction to give the corresponding isocyanates, optionally after adjusting the amount of solvent by adding additional solvent or by removing part of the solvent or by complete solvent exchange, optionally after removal of the acid, for example, by aqueous extraction or distillation.

The thermal cleavage of the polyphenyl polymethylene polycarbamates obtained by the method variant described above can be carried out as described, for example, in EP-A 1 259 480, WO 98/54128, WO 2011/051314 and WO 2011/089098 A1. The thermolysis of the amine- and urea-free urethane or amine-free urethane comprising higher-substituted ureas is generally carried out in a solvent having a boiling point of >100° C. The solvents used are preferably aromatic solvents liquid at room temperature such as toluene, xylene, benzene, chlorobenzene, dichlorobenzene, mesitylene, chlorotoluene, dichlorotoluenes, trichlorobenzenes, tetrachlorobenzenes and particularly preferably chlorinated aromatic solvents such as dichlorobenzenes, trichlorobenzenes, tetrachlorobenzenes and dichlorotoluenes. In principle, the cleavage can also be carried out on the carbonate of the precursor.

The reaction is effected at atmospheric pressure but can also be carried out under reduced pressure or positive pressure. The cleavage can be carried out either continuously or batchwise, but preferably continuously. The reaction is preferably conducted by continuously shifting the chemical equilibrium by continuously removing the liberated alcohol. The thermolysis of the urethane is generally effected in a dilution of 3 to 30% by weight in a solvent, preferably in a dilution of 7 to 25% by weight and particularly preferably between 10 and 20% by weight. The residence time of the reaction mixture in the thermolysis is from 30 to 300 minutes, preferably from 45 to 240 minutes and particularly preferably from 60 to 180 minutes.

A stabilizer may be added to the solution comprising pMDU and solvent. Such stabilizers are described, for example, in U.S. Pat. No. 4,388,246. These compounds are organic chlorine-containing compounds such as acid chlorides, carbamoyl chlorides, iron complexes and N-methyl-N-phenylcarbamoyl chloride. The compounds are added at 0.05 to 10 mol %, preferably 0.1 to 5 mol % and particularly preferably 0.2 to 2 mol %, based on pMDU used.

The resulting pMDI is then generally freed of the solvent. The solvent evaporation is generally carried out under vacuum in several stages in order to reduce the thermal decomposition of NCO groups. The residual solvent content is generally below 100 ppm by weight.

The invention is illustrated by the following examples.

EXAMPLE 1

Using a four-necked flask equipped with stirrer, reflux condenser, internal thermometer and protective gas line, 53.1 g (corresponds to 531 mmol of amino groups) of pMDA, 53.4 g (555.7 mmol) of sodium isobutoxide, 99.3 g (1339.7 mmol) of isobutanol and 184.7 g (1060 mmol) of diisobutyl carbonate were successively weighed into the flask under argon and the flask dipped into an oil bath pre-heated to 125° C. After the mixture had been stirred at this temperature for 6 h, it was cooled to 90° C., 530 ml of toluene were added, the mixture cooled to 50° C. and 265 ml of water then added. Following phase separation, the upper organic phase was washed once with 265 ml of water at approx. 50° C. and the aqueous phase back-extracted twice with 140 ml of toluene each time. Finally, the organic phase was then successively washed with 265 ml of citrate buffer (pH=5) and 275 ml of water respectively. For analytical purposes, 65 g of the organic phase were concentrated to dryness and subsequently dried for 3 h at 130° C. in an oil-pump vacuum. 6.3 g of crude urethane were thereby obtained in the form of a beige solid still comprising, according to analysis by $^1$H-NMR, approximately 2% of unreacted amino groups. This resulted in a residue content of approx. 10.6 mmol of unreacted amino groups for the overall mixture.

From the remaining organic phase, approx. 500 ml of solvent were removed under reduced pressure and the remainder dried over sodium sulfate and filtered. 3.8 g of isobutyl chloroformate (approx. 26.6 mmol) were added at 60° C. to the remaining solution containing approx. 88 g of crude urethane in diisobutyl carbonate and toluene, the resulting mixture was stirred at 60° C. for 60 min and 100 ml of water were subsequently added and the mixture stirred at 60° C. for one hour. After phase separation, the organic phase was washed three times each with 100 ml of water and once with 100 ml of saturated sodium bicarbonate solution, the organic phase concentrated to dryness under reduced pressure at 130° C. for three hours in an oil-pump vacuum. 97.5 g of purified pMDU were thereby obtained as an amber-coloured solid in which free amino groups were no longer detected by means of $^1$H-NMR and HPLC analysis.

16.1 g of purified pMDU (corresponds to 80.7 mmol as the urethane or amino groups or nitrogen equivalents present derivatized with isobutyl chloroformate), 146 g of 1,2,3,4-tetrachlorobenzene, 199 g of 1,2,4-trichlorobenzene and 163 mg (0.80 mmol) of terephthaloyl chloride were charged in a 500 ml four-necked flask equipped with stirrer, internal thermometer, and a 30 cm column with reflux condenser with packings of 5 mm wire mesh rings, protective gas line and distillation receiver and the mixture was heated to boiling by means of a heating mantle. At the time point of the first decrease of distillate, a total of 138 g of a mixture of isobutanol and solvent was distilled off over 150 minutes, whereupon the bottom temperature increased from 232° C. to 246° C. The yield of NCO determined by titration at this time point was 98.7% (based on amino groups or nitrogen equivalents in the pMDA).

The reaction output (191 g) was concentrated to 11.6 g over 45 minutes on a distillation apparatus at 70 to 110° C. distillation temperature, 0.4 mbar and an oil bath temperature of 114° C. The output from the first distillation was concentrated in a Kugelrohr apparatus at 95° C. and 0.01 mbar over 80 minutes, whereupon 9.2 g of output was obtained. Analysis by titration resulted in an NCO number of 29.1 g/100 g. No indications of carbodiimides and/or uretonimines and ureas could be found in the NMR and IR spectrum. No indications of the compounds 1 to 6 could be found in the HRMS. This resulted in a chlorine value EHC of 460 ppm.

EXAMPLE 2

50.1 g (corresponds to 500 mmol of amino groups) of pMDA, 50.5 g (525 mmol) of sodium isobutoxide, 93.9 g (1270 mmol) of isobutanol and 174 g (1000 mmol) of diisobutyl carbonate were successively weighed under argon into a 2000 ml four-necked flask equipped with stirrer, reflux condenser, internal thermometer and protective gas line and the flask dipped into an oil bath pre-heated to 125° C. After the mixture had been stirred at this temperature for 6 h, it was diluted with 500 ml of toluene, the mixture cooled to 50° C. and 300 ml of water then added. After phase separation, the upper organic phase was washed once with 250 ml of water. The aqueous phases were back-extracted twice with 250 ml of toluene each time and all the organic phases were combined. Finally, the organic phases were successively washed with 250 ml of citrate buffer (pH=5) and 250 ml of water respectively and concentrated to dryness under reduced pressure. 104 g of crude urethane were thereby obtained in the form of a beige solid still comprising, according to analysis by 1H-NMR, approximately 12 mmol of unreacted amino groups.

44.5 g of crude urethane were dissolved in 300 g of HCl-saturated chlorobenzene/isobutanol mixture (95:5 v/v) and filtered through a 14 cm high bed of silca gel (0.040 to 0.063 mm particle size) with a diameter of 8 cm. The column was rinsed with the abovementioned mixture until all urethanes had been eluted. Finally, the pMDU-containing filtrate was washed five times each with 200 ml of water and concentrated to dryness under reduced pressure. 38.1 g of purified pMDU were thereby obtained as a slightly brownish solid in which no free amino groups were detected by means of $^1$H-NMR and HPLC analysis.

25.0 g of purified pMDU (corresponds to 124 mmol of amino groups removed by filtration), 146 g of 1,2,3,4-tetrachlorobenzene and 199 g of 1,2,4-trichlorobenzene were charged in a 500 ml four-necked flask equipped with stirrer, internal thermometer, and a 30 cm column with reflux condenser with packings of 5 mm wire mesh rings, protective gas line and distillation receiver and the mixture was heated to boiling by means of a heating mantle. At the time point of the first decrease of distillate, a total of 75.5 g of a mixture of isobutanol and solvent had been distilled off over 3 h, whereupon the bottom temperature increased from 232° C. to 240° C. The yield of NCO determined by titration at this time point was 83% (based on amino groups in the pMDA). The ratio V of the respective signal strengths determined by IR spectroscopy after a total of 4 h, which were determined for the absorption bands of the carbodiimide Hlmid and the isocyanate functionalities Hlso, V=Hlmid/Hlso was 0.21.

COMPARATIVE EXAMPLE 1

50.1 g (corresponds to 500 mmol of amino groups) of pMDA were reacted according to example 2. 117 g of crude urethane were thereby obtained in the form of a beige solid still comprising, according to analysis by $^1$H-NMR, approximately 14 mmol of unreacted amino groups. This crude product was used directly in the subsequent thermolysis without further treatment.

25.0 g of crude pMDU (corresponds to 124 mmol of amino groups not removed by filtration) was reacted according to example 1. At the time point of the first decrease of distillate, a total of 81.7 g of a mixture of isobutanol and solvent had been distilled off over 4 h, whereupon the bottom temperature increased from 232° C. to 238° C. The yield of NCO determined by titration at this time point was 50% (based on amino groups in the pMDA). The ratio V of the respective signal strengths determined by IR, which were determined for the absorption bands of the carbodiimide $H_{Imid}$ and the isocyanate functionalities $H_{Iso}$, V=$H_{Imid}$/

$H_{Iso}$ was 0.40, which demonstrates the significantly reduced selectivity of the reaction in the presence of unremoved amino groups.

COMPARATIVE EXAMPLE 2

50.1 g (corresponds to 500 mmol of amino groups) of pMDA were reacted according to example 2. 116 g of crude urethane were thereby obtained in the form of a beige solid still comprising, according to analysis by $^1$H-NMR, approximately 12 mmol of unreacted amino groups. 57.2 g of crude urethane were dissolved in 324 g of chlorobenzene/isobutanol mixture (95:5 v/v) and filtered through a 14 cm high bed of silica gel (0.040 to 0.063 mm particle size) with a diameter of 8 cm. The column was rinsed with the above-mentioned mixture until all urethanes had been eluted. Finally, the pMDU-containing filtrate was concentrated to dryness under reduced pressure. 50.1 g of purified pMDU were thereby obtained in the form of a beige solid still comprising, according to analysis by $^1$H-NMR, approximately 3 mmol of unreacted amino groups.

25.0 g of crude pMDU (corresponds to 125 mmol of amino groups not removed by filtration) was reacted according to example 2. At the time point of the first decrease of distillate, a total of 69.7 g of a mixture of isobutanol and solvent had been distilled off over 4 h, whereupon the bottom temperature increased from 232° C. to 237° C. The yield of NCO determined by titration at this time point was 59% (based on amino groups in the pMDA). The ratio V of the respective signal strengths determined by IR spectroscopy, which were determined for the absorption bands of the carbodiimide $H_{Imid}$ and the isocyanate functionalities $H_{Iso}$, $V=H_{Imid}/H_{Iso}$ was 0.32, which demonstrates the reduced selectivity of the reaction in the presence of incompletely removed amino groups.

EXAMPLE 3

50.0 g (corresponds to 500 mmol of amino groups) of pMDA, 50.5 g (525 mmol) of sodium isobutoxide, 93.7 g (1264 mmol) of isobutanol and 174 g (1000 mmol) of diisobutyl carbonate were successively weighed under argon into a 2000 ml four-necked flask equipped with stirrer, reflux condenser, internal thermometer and protective gas line and the flask dipped into an oil bath pre-heated to 125° C. After the mixture had been stirred at this temperature for 6 h, it was diluted with 500 ml of toluene, the mixture cooled to 50° C. and 300 ml of water then added. After phase separation, the upper organic phase was washed once with 250 ml of water. The aqueous phases were back-extracted twice with 250 ml of toluene each time and all the organic phases were combined. Finally, the organic phases were successively washed with 250 ml of citrate buffer (pH=5) and 250 ml of water respectively and concentrated to dryness under reduced pressure. 99.1 g of crude urethane were thereby obtained in the form of a beige solid still comprising, according to analysis by 1H-NMR, approximately 10 mmol of unreacted amino groups.

34.9 g of crude urethane were dissolved in 246 g of HCl-saturated chlorobenzene/isobutanol mixture (95:5 v/v) and filtered through a 15 cm high bed of silica gel (0.040 to 0.063 mm particle size) with a diameter of 8 cm. The column was rinsed with the abovementioned mixture until all urethanes had been eluted. Finally, the pMDU-containing filtrate was washed five times each with 200 ml of water and concentrated to dryness under reduced pressure. 30.4 g of purified pMDU were thereby obtained as a slightly brownish solid in which no free amino groups were detected by means of $^1$H-NMR and HPLC analysis.

21.7 g of purified pMDU 0.159 g of dibutyltin dilaurate, 146 g of 1,2,3,4-tetrachlorobenzene and 200 g of 1,2,4-trichlorobenzene were charged in a 500 ml four-necked flask equipped with stirrer, internal thermometer, and a 30 cm column with reflux condenser with packings of 5 mm wire mesh rings, protective gas line and distillation receiver and the mixture was heated to boiling by means of a heating mantle. At the time point of the first decrease of distillate, a total of 141.4 g of a mixture of isobutanol and solvent had been distilled off over 4 h, whereupon the bottom temperature increased from 232° C. to 247° C. The yield of NCO determined by titration at this time point was 29% (based on amino groups in the pMDA).

COMPARATIVE EXAMPLE 3

50.1 g (corresponds to 500 mmol of amino groups) of pMDA, 50.5 g (525 mmol) of sodium isobutoxide, 93.7 g (1264 mmol) of isobutanol and 174 g (1000 mmol) of diisobutyl carbonate were reacted with one another according to example 2. 99 g of crude urethane were thereby obtained in the form of an orange solid still comprising, according to analysis by $^1$H-NMR, approximately 9 mmol of unreacted amino groups. This crude product was used directly in the subsequent thermolysis without further treatment.

25.0 g of crude pMDU (corresponds to 125 mmol of unremoved amino groups) were reacted according to example 2 with addition of 0.2 mol % di-n-butyltin dilaurate (with respect to the amount of urethane used). At the time point of the first decrease of distillate, a total of 144.8 g of a mixture of isobutanol and solvent had been distilled off over 4 h, whereupon the bottom temperature increased from 230'C to 241° C. The yield of NCO determined by titration at this time point was 36% (based on amino groups in the pMDA). The ratio V of the respective signal strengths determined by IR spectroscopy, which were determined for the absorption bands of the carbodiimide $H_{Imid}$ and the isocyanate functionalities $H_{Iso}$, $V=H_{Imid}/H_{Iso}$ was 0.38, which demonstrates the reduced selectivity of the reaction in the presence of underivatized amino groups.

EXAMPLE 4

75.1 g (corresponds to 750 mmol of amino groups) of pMDA, 75.7 g (788 mmol) of sodium isobutoxide, 141 g (1900 mmol) of isobutanol and 261 g (1500 mmol) of diisobutyl carbonate were reacted with one another according to example 2. 145 g of crude urethane were thereby obtained in the form of a beige solid still comprising, according to analysis by $^1$H-NMR, approximately 25 mmol of unreacted amino groups.

44.5 g of crude urethane were dissolved in 121 g of HCl-saturated chlorobenzene/isobutanol mixture (95:5 v/v) and filtered through a 14 cm high bed of acidic aluminum oxide (0.063 to 0.200 mm particle size) with a diameter of 8 cm. The column was rinsed with the above-mentioned mixture until all urethanes had been eluted. Finally, the pMDU-containing filtrate was washed five times each with 200 ml of water and concentrated to dryness under reduced pressure. 36.3 g of purified pMDU were thereby obtained as a yellowish solid in which free amino groups were no longer detected by means of $^1$H-NMR and HPLC analysis.

EXAMPLE 5

44.9 g of crude urethane from example 4 were dissolved in 205 g of chlorobenzene/isobutanol mixture (95:5 v/v)

with 0.5% by weight of methanesulphonic acid and filtered through a 14 cm high bed of silica gel (0.040 to 0.063 mm particle size) with a diameter of 8 cm. The column was rinsed with the abovementioned mixture until all urethanes had been eluted. Finally, the pMDU-containing filtrate was washed five times each with 200 ml of water and concentrated to dryness under reduced pressure. 35.5 g of purified pMDU were thereby obtained as a yellow-orange solid in which free amino groups were no longer detected by means of 1H-NMR and HPLC analysis.

EXAMPLE 6

75.1 g (corresponds to 750 mmol of amino groups) of pMDA, 75.6 g (787 mmol) of sodium isobutoxide, 141 g (1900 mmol) of isobutanol and 261 g (1500 mmol) of diisobutyl carbonate were successively weighed under argon into a 2000 ml four-necked flask equipped with stirrer, reflux condenser, internal thermometer and protective gas line and the flask dipped into an oil bath pre-heated to 125° C. After the mixture had been stirred at this temperature for 6 h, it was diluted with 750 ml of toluene, the mixture cooled to 50° C. and 450 ml of water then added. After phase separation, the upper organic phase was washed once with 375 ml of water. The aqueous phases were back-extracted twice with 375 ml of toluene each time and all the organic phases were combined. Finally, the organic phases were successively washed with 375 ml of citrate buffer (pH=5) and 375 ml of water respectively and concentrated to dryness under reduced pressure. 145 g of crude urethane were thereby obtained in the form of a beige solid still comprising, according to analysis by $^1$H-NMR, approximately 29 mmol of unreacted amino groups.

7.15 g of acetic anhydride (70.0 mmol) were added to a solution of 140 g of crude urethane in 522 g of chlorobenzene and 58.0 g of 1,2,4-trichlorobenzene at 50° C., the resulting mixture stirred at 100° C. for 60 min and subsequently concentrated to dryness under reduced pressure. 141 g of purified pMDU were thereby obtained as a slightly brownish solid in which no free amino groups were detected by means of $^1$H-NMR and HPLC analysis.

25.0 g of purified pMDU (corresponds to 125 mmol as the urethane or amino groups or nitrogen equivalents present derivatized with acetic anhydride), 146 g of 1,2,3,4-tetrachlorobenzene and 199 g of 1,2,4-trichlorobenzene were charged in a 500 ml four-necked flask equipped with stirrer, internal thermometer, and a 30 cm column with reflux condenser with packings of 5 mm wire mesh rings, protective gas line and distillation receiver and the mixture was heated to boiling by means of a heating mantle. At the time point of the first decrease of distillate, a total of 81.1 g of a mixture of isobutanol and solvent had been distilled off over 3 h, whereupon the bottom temperature increased from 233° C. to 241° C. The yield of NCO determined by titration at this time point was 66% (based on amino groups or nitrogen equivalents in the pMDA). The ratio V of the respective signal strengths determined by IR spectroscopy after a total of 4 h, which were determined for the absorption bands of the carbodiimide $H_{Imid}$ and the isocyanate functionalities $H_{Iso}$, ($V=H_{Imid}/H_{Iso}$) was 0.19.

COMPARATIVE EXAMPLE 4

50.1 g (corresponds to 500 mmol of amino groups) of pMDA, 50.5 g (525 mmol) of sodium isobutoxide, 93.9 g (1270 mmol) of isobutanol and 174 g (1000 mmol) of diisobutyl carbonate were reacted with one another according to example 6. 117 g of crude urethane were thereby obtained in the form of a beige solid still comprising, according to analysis by $^1$H-NMR, approximately 14 mmol of unreacted amino groups. This crude product was used directly in the subsequent thermolysis without further treatment.

25.0 g of crude pMDU (corresponds to 125 mmol as the urethane or amino groups or nitrogen equivalents present underivatized) were heated to boiling point in tetrachlorobenzene/trichlorobenzene according to example 6. At the time point of the first decrease of distillate, a total of 81.7 g of a mixture of isobutanol and solvent had been distilled off over 4 h, whereupon the bottom temperature increased from 232° C. to 238° C. The yield of NCO determined by titration at this time point was 50% (based on amino groups or nitrogen equivalents in the pMDA). The ratio V of the respective signal strengths determined by IR spectroscopy, which were determined for the absorption bands of the carbodiimide $H_{Imid}$ and the isocyanate functionalities $H_{Iso}$, ($V=H_{Imid}/H_{Iso}$) was 0.40, which demonstrates the reduced selectivity of the reaction in the presence of underivatized amino groups.

EXAMPLE 7

8.00 g of purified pMDU from example 6 (corresponds to 40 mmol as the urethane according to example 6 or amino groups or nitrogen equivalents present derivatized with acetic anydride) was heated to boiling point in tetrachlorobenzene/trichlorobenzene as described in example 6 in the presence of 51 mg (0.080 mmol) of di-n-butyltin dilaurate. At the time point of the first decrease of distillate, a total of 35.0 g of a mixture of isobutanol and solvent had been distilled off over 60 min, whereupon the bottom temperature increased from 234° C. to 236° C. The yield of NCO determined by titration at this time point was 91% (based on amino groups or nitrogen equivalents in the pMDA). The ratio V of the respective signal strengths determined by IR spectroscopy after a total of 4 h, which were determined for the absorption bands of the carbodiimide $H_{Imid}$ and the isocyanate functionalities $H_{Iso}$, ($V=H_{Imid}/H_{Iso}$) was 0.13.

COMPARATIVE EXAMPLE 5

50.0 g (corresponds to 500 mmol of amino groups) of pMDA, 50.5 g (525 mmol) of sodium isobutoxide, 93.7 g (1260 mmol) of isobutanol and 174.2 g (1000 mmol) of diisobutyl carbonate were reacted with one another according to example 6. 99.1 g of crude urethane were thereby obtained in the form of an orange solid still comprising, according to analysis by $^1$H-NMR, approximately 10 mmol of unreacted amino groups. This crude product was used directly in the subsequent thermolysis without further treatment.

8 g of crude pMDU (corresponds to 40.3 mmol as the urethane or amino groups or nitrogen equivalents present underivatized) were heated to boiling point in tetrachlorobenzene/trichlorobenzene as described in example 6 in the presence of 0.2 mol % di-n-butyltin dilaurate (with respect to the amount of urethane used). At the time point of the first decrease of distillate, a total of 139.7 g of a mixture of isobutanol and solvent had been distilled off over 4 h, whereupon the bottom temperature increased from 230° C. to 249° C. The yield of NCO determined by titration at this time point was 47% (based on amino groups or nitrogen equivalents in the pMDA). The ratio V of the respective signal strengths determined by IR spectroscopy, which were determined for the absorption bands of the carbodiimide H$_{Imid}$ and the isocyanate functionalities H$_{Iso}$, (V=H$_{Imid}$/H$_{Iso}$) was 0.38, which demonstrates the reduced selectivity of the reaction in the presence of underivatized amino groups.

EXAMPLE 8

75.1 g (corresponds to 750 mmol of amino groups) of pMDA were reacted according to example 6. 145 g of crude urethane were thereby obtained in the form of a beige solid still comprising, according to analysis by $^1$H-NMR, approximately 24 mmol of unreacted amino groups.

5.49 g of acetyl chloride (70.0 mmol) were added to a solution of 140 g of crude urethane in 522 g of chlorobenzene and 58.0 g of 1,2,4-trichlorobenzene at 50° C., the resulting mixture stirred at 50° C. for 60 min and subsequently concentrated to dryness under reduced pressure. 140 g of purified pMDU were thereby obtained as a slightly brownish solid in which no free amino groups were detected by means of $^1$H-NMR and HPLC analysis.

25.0 g of purified pMDU (corresponds to 126 mmol as the urethane or amino groups or nitrogen equivalents present derivatized with acetic anhydride) were reacted according to example 6. At the time point of the first decrease of distillate, a total of 81.5 g of a mixture of isobutanol and solvent had been distilled off over 3 h, whereupon the bottom temperature increased from 233° C. to 240° C. The yield of NCO determined by titration at this time point was 75% (based on amino groups or nitrogen equivalents in the pMDA). The ratio V of the respective signal strengths determined by IR spectroscopy after a total of 4 h, which were determined for the absorption bands of the carbodiimide H$_{Imid}$ and the isocyanate functionalities H$_{Iso}$, (V=H$_{Imid}$/H$_{Iso}$) was 0.26.

EXAMPLE 9

75.1 g (corresponds to 750 mmol of amino groups) of pMDA were reacted according to example 6. 152 g of crude urethane were thereby obtained in the form of a beige solid still comprising, according to analysis by $^1$H-NMR, approximately 20 mmol of unreacted amino groups.

1.84 g of succinyl dichloride (11.9 mmol) were added to a solution of 24.0 g of crude urethane in 250 g of toluene at 50° C., the resulting mixture stirred at 100° C. for 60 min and subsequently concentrated to dryness under reduced pressure. 24.0 g of purified pMDU were thereby obtained as a slightly brownish solid in which no free amino groups were detected by means of $^1$H-NMR and HPLC analysis.

8.0 g of purified pMDU (corresponds to 40 mmol of reacted amino groups or nitrogen equivalents according to the description above) were reacted according to example 6. At the time point of the first decrease of distillate, a total of 129 g of a mixture of isobutanol and solvent had been distilled off over 4 h, whereupon the bottom temperature increased from 231° C. to 247° C. The yield of NCO determined by titration at this time point was 87% (based on amino groups or nitrogen equivalents in the pMDA). The ratio V of the respective signal strengths determined by IR spectroscopy after a total of 4 h, which were determined for the absorption bands of the carbodiimide H$_{Imid}$ and the isocyanate functionalities H$_{Iso}$, (V=H$_{Imid}$/H$_{Iso}$) was 0.31.

The invention claimed is:

1. A method for preparing a polyphenyl polymethylene polyisocyanate having an NCO number, determined according to DIN EN ISO 14896, of at least 29% comprising less than 2% by weight ureas, determined by NMR, less than 8% by weight carbodiimides or uretonimines, determined by NMR, and less than 1000 ppm organic chlorine compounds, determined by high-resolution mass spectrometry or according to ASTM D4663-10, the method comprising:
   reacting a polyphenyl polymethylene polyamine with an organic carbonate to give a corresponding polyphenyl polymethylene polycarbamate;
   thermally cleaving the polyphenyl polymethylene polycarbamate to give the polyphenyl polymethylene polyisocyanate; and
   prior to the thermally cleaving, reacting free amino groups or urea groups present in a carbamate crude mixture comprising the polyphenyl polymethylene polycarbamate with a derivatizing reagent to give amide groups or urethane groups.

2. The method according to claim 1, wherein the derivatizing reagent is at least one selected from the group consisting of an ester, an acid anhydride, and an acyl chloride of an aliphatic carboxylic acid having 1 to 10 carbon atoms or an aromatic carboxylic acid having 7 to 14 carbon atoms.

3. The method according to claim 1, wherein the derivatizing reagent comprises at least one of acetic anhydride and acetyl chloride.

4. The method according to claim 1, wherein the derivatizing reagent comprises at least one of a chlorothrmic ester and a pyrocarbonate of C$_1$-C$_8$-alkanols.

5. The method according to claim 1, wherein the reacting of the free amino groups or the urea groups with the derivatizing reagent is carried out in a solvent.

6. The method according to claim 5, wherein the solvent is at least one of an aromatic hydrocarbon and a chlorohydrocarbon having 6 to 20 carbon atoms.

7. The method according to claim 1, wherein the thermally cleaving of the polyphenyl polymethylene polycarbamate is effected by heating in a solvent to a temperature of 180 to 300° C.

8. The method according to claim 7, wherein the solvent is at least one of an aromatic hydrocarbon or a chlorohydrocarbon having 6 to 20 carbon atoms.

9. The method according to claim 1, wherein N-arylcarbamate is prepared by reacting an aromatic amine with a dialkyl carbonate in the presence of bases and hydrolysis of a resulting metal carbamate.

10. The method according to claim 9, wherein the dialkyl carbonate is at least one selected from the group consisting of diethyl carbonate, di-n-propyl carbonate, di-n-butyl carbonate, di-2-methylpropyl carbonate, di-3-methylbutyl carbonate, di-n-pentyl carbonate, bis-2-methoxyethyl carbonate, bis-2-ethoxyethyl carbonate, bis-2,2,2-trifluoroethyl carbonate and diisobutyl carbonate.

* * * * *

UNITED STATES PATENT AND TRADEMARK OFFICE
CERTIFICATE OF CORRECTION

PATENT NO. : 10,501,406 B2
APPLICATION NO. : 15/546871
DATED : December 10, 2019
INVENTOR(S) : Michael Lorenz et al.

It is certified that error appears in the above-identified patent and that said Letters Patent is hereby corrected as shown below:

On the Title Page

Item (57), Abstract, Line 15, "carhamate" should read -- carbamate --.

In the Specification

In Column 1, Line 25, "(NF" should read -- (A/F --.

In Column 2, Lines 13-14, "monochlorobenezene," should read -- monochlorobenzene, --.

In Column 5, Line 4, "commerical" should read -- commercial --.

In Column 7, Line 37, "di-2-methyl propyl" should read -- di-2-methylpropyl --.

In Column 9, Line 53, "urethaneforming" should read -- urethane-forming --.

In Column 10, Line 47, "Brönstedt" should read -- Brønsted --.

In Column 10, Line 59, "waterglass" should read -- water glass --.

In Column 10, Lines 60-61, "Hollemann" should read -- Holleman --.

In Column 11, Line 51, "Brönstedt" should read -- Brønsted --.

In Column 11, Lines 62-63, "paratoluenesulfonic" should read -- para-toluenesulfonic --.

In Column 14, Line 14, "1H-NMR," should read -- $^1$H-NMR, --.

In Column 14, Line 18, "silca" should read -- silica --.

Signed and Sealed this
Fourth Day of August, 2020

Andrei Iancu
*Director of the United States Patent and Trademark Office*

CERTIFICATE OF CORRECTION (continued)
U.S. Pat. No. 10,501,406 B2

In Column 14, Line 44, "Hlmid" should read -- $H_{lmid}$ --.

In Column 14, Lines 44-45, "Hlso, V=Hlmid/Hlso" should read -- $H_{lso}$, V=$H_{lmid}$/$H_{lso}$ --.

In Column 15, Line 57, "1H-NMR," should read -- $^1$H-NMR, --.

In Column 16, Line 34, "230'C" should read -- 230° C. --.

In Column 17, Line 10, "1H-NMR" should read -- $^1$H-NMR --.

In Column 18, Line 29, "anydride)" should read -- anhydride) --.

In Column 19, Line 2, "Hlmid" should read -- $H_{lmid}$ --.

In the Claims

In Column 20, Line 33, Claim 4, "chlorothrmic" should read -- chloroformic --.